(12) United States Patent
Chi et al.

(10) Patent No.: US 6,500,440 B1
(45) Date of Patent: Dec. 31, 2002

(54) TOPICAL PREPARATION OF ALPROSTADIL FOR THE TREATMENT OF ERECTILE DYSFUNCTION

(75) Inventors: Sang-Cheol Chi, Suwon-si (KR); Dong Soo Lee, Pyoungtaek-si (KR); Kye Kwan Lee, Suwon-si (KR)

(73) Assignee: Whan In Pharm Co., Ltd., Seoul (KR)

( * ) Notice: Subject to any disclaimer, the term of this patent is extended or adjusted under 35 U.S.C. 154(b) by 0 days.

(21) Appl. No.: 09/649,059

(22) Filed: Aug. 29, 2000

(30) Foreign Application Priority Data

Jun. 23, 2000 (KR) ............................................ 00-34767

(51) Int. Cl.$^7$ ................................................. A61K 7/00
(52) U.S. Cl. ........................................ 424/401; 514/273
(58) Field of Search ............................ 424/401; 514/573

(56) References Cited

U.S. PATENT DOCUMENTS

| | | | |
|---|---|---|---|
| 5,380,760 A | 1/1995 | Wendel et al. | 514/573 |
| 5,741,511 A | 4/1998 | Lee et al. | 424/449 |
| 5,942,545 A * | 8/1999 | Samour et al. | 514/573 |
| 5,952,361 A * | 9/1999 | Dias Nahoum | 524/396 |
| 6,013,277 A | 1/2000 | Curri | 424/450 |
| 6,031,002 A | 2/2000 | Wysor et al. | 514/573 |
| 6,036,977 A | 3/2000 | Drizen et al. | 424/488 |
| 6,046,240 A | 4/2000 | See | 514/573 |
| 6,046,244 A * | 4/2000 | Buyuktimkin et al. | 514/785 |

FOREIGN PATENT DOCUMENTS

WO    WO 99/66870    12/1999

OTHER PUBLICATIONS

McVary, K.T. et al., "Topical Prostaglandin E1 SEPA Gel For The Treatment of Erectile Dysfunction", The Journal of Urology, vol. 162, pp. 726–731, (1999).

Kwon, S.Y, et al., "Formulation of Topical Preparation Containing Alprostadil", Master Thesis, Sungkyunkwan University, Kyunggi–do, Republic of Korea, pp. 1–101, (1998).

* cited by examiner

Primary Examiner—Jose' G. Dees
Assistant Examiner—Konata M. George
(74) Attorney, Agent, or Firm—Finnegan, Henderson, Farabow, Garrett & Dunner LLP

(57) ABSTRACT

The present invention relates to a composition of topical preparation containing alprostadil, which has excellent skin permeation rate with little skin irritation, which is prepared by dissolving alprostadil or a solid dispersion thereof prepared using poloxamer, into a mixture of an oily vehicle, a pyrrolidone and an anti-irritant agent.

7 Claims, 1 Drawing Sheet

TOPICAL PREPARATION OF ALPROSTADIL FOR THE TREATMENT OF ERECTILE DYSFUNCTION

FIELD OF THE INVENTION

This invention relates to a composition of topical preparation containing alprostadil for the treatment of erectile dysfunction, which has excellent skin permeation rate with little skin irritation. Particularly, the present invention relates to a composition of topical preparation containing alprostadil, which is prepared by dissolving alprostadil itself or a solid dispersion thereof prepared using poloxamer, into a mixture of an oily vehicle, a pyrrolidone and an anti-irritant agent.

PRIOR ARTS

Erectile dysfunction refers to a condition of the inability to achieve and maintain penile erection sufficient to complete satisfactory sexual intercourse. There are two major causes for the erectile dysfunction: psychogenic and organic causes. Previously, erectile dysfunction was thought to be of psychogenic origin. In these days, however, it is believed that most of erectile dysfunction comes from organic causes resulting from damage in nerve, blood vessel or hormone system, surgery, or drug administration.

Erectile dysfunction can be cured with surgical or pharmacological means. For the pharmacological treatment, some effective drugs are available, orally or locally. As oral drugs, yohimbine and trazodone have been used, but their clinical effect is not pronounced. Recently, sildenafil, a selective inhibitor of phosphodiesterase, has been introduced into the market as an oral drug. This new oral drug showed positive result in the treatment of erectile dysfunction. However, the oral administration of a drug accompanies systemic side effects inevitably, since the drug reaches the site of action after it is distributed throughout the whole body by the systemic circulation. Sildenafil also has some systemic side effects such as headache, flushing, indigestion and changes in vision, etc. Particularly, it may cause a serious side effect, if taken by patient medicated with organic nitrates, due to the possibility of dramatic drop in blood pressure. Therefore, a local treatment is the method of choice for the treatment of erectile dysfunction, since it is a local disorder. For this purpose, alprostadil (prostaglandin E1), papaverine, or phentolamine has been used. Among them, alprostadil is demonstrated to be the most effective drug for the local treatment of erectile dysfunction. Until now, intracavernous injection and transurethral pellet of alprostadil are commercially available in the market. However, the injection formulation needs a direct injection to the penis. Thus, patients may feel uncomfortable, and a pain or bleeding, or even infection on the injected site may occur. The transurethral pellet also has inconvenience in inserting into urethra, and burning sense on urethra or pain on penis may occur.

As mentioned above, alprostadil shows excellent pharmacological effect in the treatment of erectile dysfunction when applied locally. However, these two invasive methods, intracavernous injection and transurethral delivery, are only available as currently available dosage forms even though a topical preparation is more convenient to apply than those methods. This is due to two problems in the formulation of alprostadil as a topical preparation. One is the instability of the drug in the conventional topical preparation which usually contains water in it. Like other prostaglandins, alprostadil is degraded easily to prostaglandin $A_1$ or prostaglandin $B_1$ in the presence of water. The other one is that the skin permeation rate of alprostadil itself is too low to achieve therapeutic drug concentration locally when applied topically.

The dosage forms for the topical application of alprostadil disclosed in patents include gels, ointments, creams without any detailed formula. Beside those dosage forms, U.S. Pat. Nos. 6,046,240 and 6,013,277 disclosed liposome for the formulation of topical preparations of alprostadil. However, all these dosage forms include water in them, which induces the degradation of alprostadil. As a dosage form which does not contain water, WO No. 99/66870, U.S. Pat. Nos. 5,380,760 and 5,741,511 disclosed transdermal patch for the topical delivery of alprostadil. However, transdermal patch has a critical drawback that it needs long time to delivery the drug underneath the skin enough to reach the therapeutic drug concentration locally. In addition, all of these patents do not mention any special enhancers for the skin permeation of alprostadil. On the other hand, U.S. Pat. Nos. 6,046,244 and 5,942,545 disclosed topical preparations of alprostadil which contain skin permeation enhancers. In U.S. Pat. No. 6,046,244, alkyl-2-(N,N-disubstituted amino)-alkanoate or (N,N-disubstituted amino)-alkanol alkanoate has been used as the skin permeation enhancer, and in U.S. Pat. No. 5,942,545, dioxolane, dioxane, or acetal. However, these enhancers are not commercially available and there are not sufficient information on the effects of these enhancers other than that as a skin permeation enhancer so far, since these are new materials. The present inventors had found that some pyrrolidones of pharmaceutical or cosmetic grade enhance the skin permeation of alprostadil, and filed a patent application for this invention (Korean Patent Application No. 99-31090). The excellent skin permeation of alprostadil was obtained with the preparation of this patent. Also, the stability of alprostadil in the preparation was highly improved, since the topical formulation in this patent is based on non-aqueous vehicles. However, the preparation in this patent has also a shortcoming of severe topical irritation on the applied area, which may be due to the drug itself or the excipients used or the combination of the two.

SUMMARY OF THE INVENTION

Through intensive research for a long time on the combination of oily vehicles, skin permeation enhancers and anti-irritant agents for the alprostadil, the present inventors discovered a composition of topical preparation containing alprostadil which has excellent skin permeation rate with little skin irritation to complete the present invention.

Therefore, an object of the present invention is to provide a composition of topical preparation containing alprostadil for the treatment of erectile dysfunction, which has excellent skin permeation rate with little skin irritation.

DETAILED DESCRIPTION OF THE INVENTION

Figure 1:
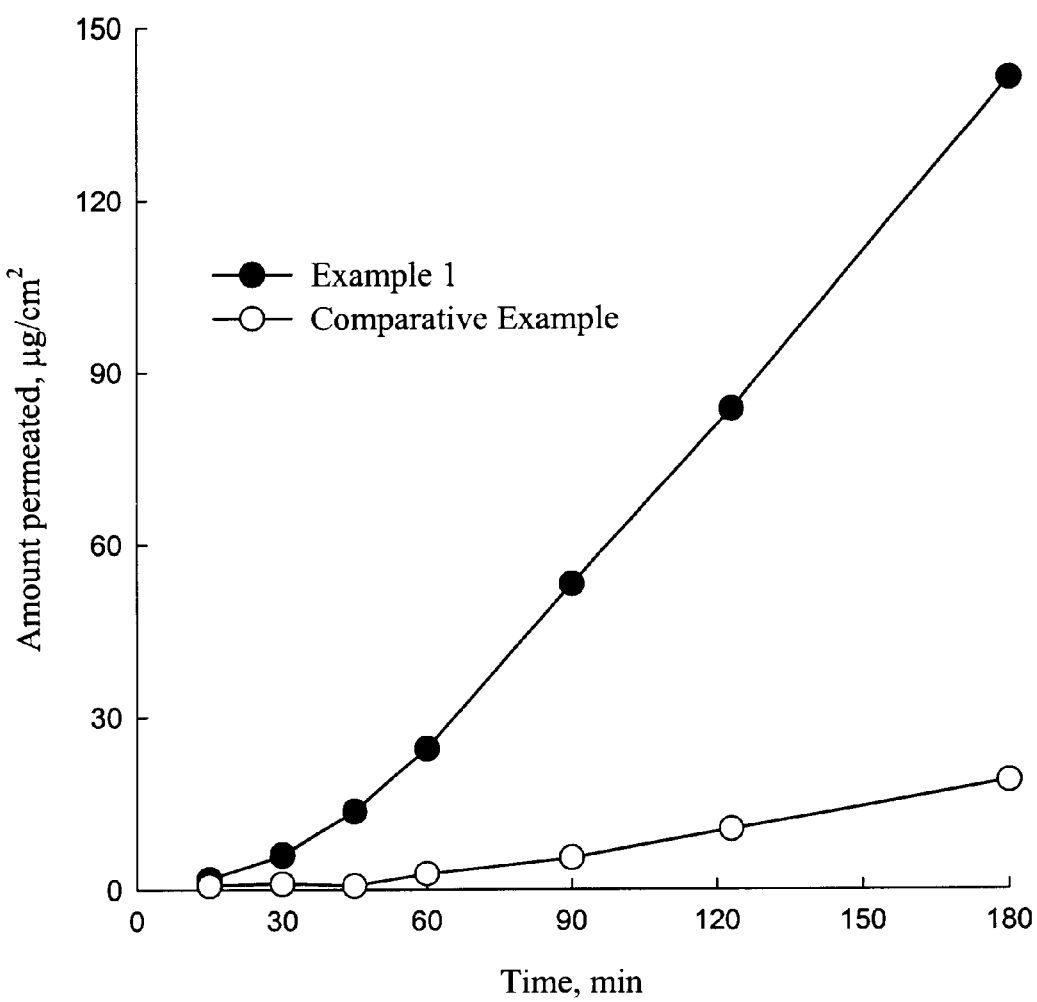
FIG. 1 shows skin permeation profiles of alprostadil from a topical gel prepared according to the present invention and a comparative composition.

The present invention provides a composition of topical preparation containing alprostadil, which is prepared by dissolving alprostadil itself or a solid dispersion thereof prepared using poloxamer, into a mixture of an oily vehicle, a pyrrolidone and an anti-irritant agent to prepare a composition.

Alprostadil, the active ingredient, is preferably in an amount of 0.1%~5% to the total weight of the composition depending on the desired strength of action. Alprostadil can be used in itself, or in a form of solid dispersion that is prepared using poloxamer to prevent possible degradation of the drug. The solid dispersion of alprostadil is prepared as follows. Poloxamer is completely melted at 90~150° C. and then alprostadil is added thereto, melted and then cooled down to room temperature. When the temperature is less than 90° C., alprostadil may not be completely dissolved into poloxamer, and when the temperature is higher than 150° C., the drug may be degraded. Examples of the poloxamer used in the present invention include at least one of poloxamer 188, poloxamer 237, poloxamer 338 and poloxamer 407, but it is not limited thereto, and may be any as long as it belongs to polyoxyethylene-polyoxypropylene copolymer. The amount of poloxamer is 1~100 weight parts to 1 weight part of alprostadil. If the amount of poloxamer in the solid dispersion is less than 1 part, it is difficult to prepare a complete solid dispersion, and if the amount is more than 100 parts, it has deleterious effect on the skin permeation of alprostadil.

Alprostadil or the solid dispersion thereof thus prepared is then dissolved into a mixture of an oily vehicle, a pyrrolidone and an anti-irritant agent to prepare a topical preparation containing alprostadil. Examples of the oily vehicle include glycerin esters of fatty acids such as mono- or tri-glycerides of fatty acids, including their polyethylene glycol complex, polyethylene glycol or propylene glycol esters of fatty acids or vegetable oils; vegetable oils, including their hydrogenated form, such as sesame oil, soybean oil, castor oil, corn oil, palm oil, peanut oil, cacao oil, cotton seed oil, sunflower seed oil, safflower oil, almond oil or olive oil; fatty acids and fatty alcohols, and their esters, such as oleic acid, linolenic acid, linoleic acid, palmitic acid, palmitoleic acid, arachidonic acid, myristic acid, capric acid, caprylic acid, lauric acid, stearic acid, lauryl alcohol, oleyl alcohol, cetyl alcohol, stearyl alcohol, ethyl oleate, oleyl laurate, isopropyl myristate, isopropyl palmitate, 2-octyldodecyl myristate or cetyl palmitate; and a mixture thereof. The amount of oily vehicle may be 20~80% to the total weight of the composition.

Pyrrolidones are employed as skin permeation enhancers to increase the skin permeation of alprostadil, and their examples include: N-methyl-2-pyrrolidone, 2-pyrrolidone, 1-octyl-pyrrolidone, 1-dodecyl-pyrrolidone, N-ethyl-2-pyrrolidone, N-cyclohexyl-2-pyrrolidone, 1-butyl-3-dodecyl-2-pyrrolidone, 1,5-dimethyl-2-pyrrolidone, 1-hexyl-2-pyrrolidone, 1-hexyl-4-methyloxycarbonyl-2-pyrrolidone, 1-(2-hydroxyethyl) pyrrolidone, 3-hydroxy-N-methyl-2-pyrrolidone, and 1-lauryl-4-methyloxycarbonyl-2-pyrrolidone.

Auxiliary skin permeation enhancers may be included into the composition of the present invention in order to further improve the skin permeation of alprostadil. Examples of the auxiliary skin permeation enhancers include: non-ionic surfactants such as polyethylene sorbitan ester, sorbitan ester or polyoxyethylene alkyl ether; terpenes such as menthol, cineol, limonene, geraniol or terpineol; and a mixture thereof.

The amount of skin permeation enhancer including its auxiliary skin permeation enhancer is 5%~70% to the total weight of the composition. If it is out of this range, it does not exhibit sufficient skin permeation.

When the topical preparation of alprostadil is applied to the gland, skin irritation may be occurred due to the drug and/or the excipients thereof. The usual symptom is redness on the applied site and in worse case, pain may be accompanied. To reduce this side effect, anti-irritant agents are included. Examples of anti-irritant agents suitable in the composition object of the present invention are squalene, squalane, avocado oil, tocopherol, polyvinyl pyrrolidone, hialulonic acid, aloevera gel, spingosine, betaglucan, rosemary oil, alantoin; topical anesthetics such as benzocaine, lidocaine, tetracaine or procaine; and a mixture thereof.

The amount of the anti-irritant agent in the formulation is preferably 1%~30% to the total weight of the composition, depending on the amount of the drug, and also the kind and amount of the excipients used. If less than 1%, it is not sufficient to decrease skin irritation, and if more than 30%, skin permeation of alprostadil may be decreased and even irritation due to the anti-irritant agent used may occur.

The apparent dosage form of the composition of alprostadil prepared as above is liquid. It can be used in itself, or its viscosity may be increased for the convenience in carrying or applying. For this purpose, Korean Patent Application No. 99-31090 has proposed the addition of colloidal silicone dioxide, but alprostadil is highly adsorbed onto this material, leading to a significant decrease in skin permeation of alprostadil. Therefore, the present invention uses a thickener instead of colloidal sillicone dioxide such as: waxes, including their derivatives, such as carnauba wax, white wax, beeswax, cetyl esters, paraffin, vaseline, lanolin or PEG-8 beeswax; metallic salts of stearic acids such as aluminum stearate, calcium stearate, magnesium stearate or zinc stearate; polyethylene, polyethylene glycol of high molecular weight, polyethylene oxide; and a mixture thereof. The thickener can be used up to 50% to the composition. If it is used more than 50%, the viscosity of the drug becomes too high for proper use.

Thus prepared topical preparation containing alprostadil has an excellent skin permeation rate as well as little skin irritation when applied locally.

The following Examples are given with the purpose of giving a better understanding of the object, characteristics, advantages and usefulness of the present invention, but never limit the scope of the present invention.

EXAMPLE 1

| | |
|---|---|
| alprostadil | 1 |
| propylene glycol caprylate/caprate | 41 |
| safflower oil | 5 |
| carnauba wax | 15 |
| N-methyl-2-pyrrolidone | 30 |
| sorbitan monooleate | 5 |
| squalene | 3 |

After 15 g of carnauba wax was melted at 90° C., a mixture of 41 g of propylene glycol caprylate/caprate and 5 g of safflower oil was added thereto and mixed completely, then cooled down to room temperature. To this mixture, 30 g of N-methyl-2-pyrrolidone, 5 g of sorbitan monooleate and 3 g of squalene were added added in order and mixed homogeneously. Then, 1 g of alprostadil was added thereto, and stirred until completely dissolved.

EXAMPLE 2

| | |
|---|---|
| alprostadil | 0.4 |
| 2-octyldodecyl myristate | 29.6 |
| beeswax | 10 |
| N-methyl-2-pyrrolidone | 40 |
| tocopherol | 20 |

After 10 g of beeswax was melted at 70° C., 29.6 g of 2-octyldodecyl myristate is added thereto and mixed completely, then cooled down to room temperature. To this mixture, 40 g of N-methyl-2-pyrrolidone and 20 g of tocopherol were added in order and mixed homogeneously. Then, 0.4 g of alprostadil was added thereto, and stirred until completely dissolved.

EXAMPLE 3

| | |
|---|---|
| alprostadil | 2 |
| isopropyl palmitate | 60 |
| safflower oil | 10 |
| 1-dodecyl-pyrrolidone | 10 |
| limonene | 3 |
| squalene | 15 |

To a premixed liquid of 60 g of isopropyl palmitate, 10 g of safflower oil, 10 g of 1-dodecyl-pyrrolidone, 3 g of limonene and 15 g of squalene, was added 2 g of alprostadil, and stirred until completely dissolved.

EXAMPLE 4

| | |
|---|---|
| alprostadil | 0.1 |
| PEG-8 caprylic/capric glycerides | 20 |
| glyceryl stearate | 30 |
| N-methyl-2-pyrrolidone | 15 |
| cineol | 9.9 |
| squalane | 25 |

To a premixed liquid of 20 g of PEG-8 caprylic/capric glycerides, 30 g of glyceryl stearate, 15 g of N-methyl-2-pyrrolidone, 9.9 g of cineol and 25 g of squalane, was added 0.1 g of alprostadil, and stirred until completely dissolved.

EXAMPLE 5

| | |
|---|---|
| alprostadil | 0.4 |
| corn oil PEG-6 ester | 31.6 |
| aluminium stearate | 50 |
| N-ethyl-2-pyrrolidone | 10 |
| menthol | 3 |
| squalene | 5 |

After 50 g of aluminium stearate was melted at 130° C., 31.6 g of corn oil PEG-6 ester was added thereto and mixed completely, then cooled down to room temperature. To this mixture, 10 g of N-ethyl-2-pyrrolidone, 5 g of squalane and 3 g of menthol were added in order and mixed homogeneously. Then, 0.4 g of alprostadil was added thereto, and stirred until completely dissolved.

EXAMPLE 6

| | |
|---|---|
| alprostadil | 1 |
| ethyl oleate | 15 |
| olive oil PEG-6 ester | 10 |
| N-ethyl-2-pyrrolidone | 40 |
| POE(5) lauryl ether | 30 |
| lidocaine | 4 |

To a premixed liquid of 15 g of ethyl oleate, 10 g of olive oil PEG-6 ester, 40 g of N-ethyl-2-pyrrolidone, 30 g of POE (5) lauryl ether and 4 g of lidocaine, was added 1 g of alprostadil, and stirred until completely dissolved.

EXAMPLE 7

| | |
|---|---|
| alprostadil | 0.5 |
| poloxamer 407 | 25 |
| propylene glycol monolaurate | 44.5 |
| almond oil | 10 |
| cetyl esters | 5 |
| N-methyl-2-pyrrolidone | 10 |
| avocado oil | 5 |

After 25 g of poloxamer 407 was melted at about 110° C., 0.5 g of alprostadil was added and mixed until completely melted, then cooled down to room temperature. Separately, after 5 g of cetyl esters was melted at 50° C., a mixture of 44.5 g of propylene glycol monolaurate and 10 g of almond oil was added and mixed completely, then cooled down to room temperature. To this mixture, 10 g of N-methyl-2-pyrrolidone and 5 g of avocado oil were added in order and mixed homogeneously. Then the alprostadil solid dispersion was added thereto, and stirred until completely dissolved.

EXAMPLE 8

| | |
|---|---|
| alprostadil | 5 |
| poloxamer 407 | 25 |
| caprylic/capric triglyceride | 36 |
| safflower oil | 6 |
| 2-pyrrolidone | 20 |
| sorbitan stearate | 7 |
| squalane | 1 |

After 25 g of poloxamer 407 was melted at about 110° C., 5 g of alprostadil was added and mixed until completely melted, and then cooled down to room temperature. To a mixture of 36 g of caprylic/capric triglyceride, 6 g of safflower oil, 20 g of 2-pyrrolidone, 7 g of sorbitan stearate and 1 g of squalane, was added the alprostadil solid dispersion and stirred until completely dissolved.

Experimental Example 1
Skin Permeation Test

The extent and rate of skin permeation of alprostadil from the topical preparation in Example 1 were determined using Franz diffusion cell fitted with excised guinea pig skin. A cream containing 0.4% alprostadil prepared according to Example 4 in U.S. Pat. No. 6,046,244 was used as a comparative example. The effective diffusion area was 1.77 $cm^2$. The receptor compartment of the diffusion cell was filled with 0.01 M phosphate buffer (pH 7.4) and its temperature was maintained at 37±0.5° C. and stirred at a constant rate of 600 rpm during the experiment. After about 3 grams of each preparation were applied on the epidermal surface of the skin, 0.2 mL of the receptor medium was withdrawn at predetermined time intervals up to 180 minutes. The amount of alprostadil permeated into the receptor medium was determined with an HPLC method. All the experiments were repeated three times. The permeation profiles of alprostadil from the two different topical preparations are shown in FIG. 1. As shown in FIG. 1, the topical gel of alprostadil prepared according to the present invention resulted in higher skin permeation profile than the comparative example. The skin permeation rate of alprostadil and lag time were calculated from these profiles and compared. While the skin permeation rate of alprostadil from the comparative example was 8.4 ug/cm$^2$/hr, that of the topical gel in Example 1 was 58.2 ug/cm$^2$/hr. This indicates that the topical gel prepared according to the present invention resulted in 7 times higher skin permeation rate than the comparative example. Also, the lag time of the topical gel prepared according to the present invention was shorter than that of the comparative example (35.5 min vs 45.0 min).

Experimental Example 2

Skin Irritation Test

The extent of irritation on skin was evaluated after the application of the topical gel of alprostadil in Example 1 onto the site of action. The topical liquid of alprostadil prepared in Example 8 in Korean Patent Application No. 99-31090 was used as a comparative example. 250 μg of each topical preparation was applied on the gland of eight subjects. At 30 minutes after the application, the extent of redness was directly observed and scored as follows: 0; no redness, 1; mild redness, 2; moderate redness, 3; severe redness, 4; severe redness with pain. As a result, the topical gel in Example 1 and the comparative example resulted in the score of 1.3±0.5 and 3.4±0.7, respectively.

What we claim is:

1. A composition of topical preparation comprising 1) 0.1~5% by weight of alprostadil; 2) 20~80% by weight of an oily vehicle; 3) 5~70% by weight of a skin permeation enhancer; 4) 1~30% by weight of an anti-irritant agent; and 5) a thickener for the composition in an amount up to 50% by weight.

2. The composition of claim 1, wherein the oily vehicle is at least one selected from the group consisting of glycerin esters of fatty acids; vegetable oils and their hydrogenated forms; fatty acids and their esters; and fatty alcohols.

3. The composition of claim 1, wherein the skin permeation enhancer is at least one selected from the group consisting of N-methyl-2-pyrrolidone, 2-pyrrolidone, 1-octyl-pyrrolidone, 1-dodecyl-pyrrolidone, N-ethyl-2-pyrrolidone, N-cyclohexyl-2-pyrrolidone, 1-butyl-3-dodecyl-2-pyrrolidone, 1,5-dimethyl-2-pyrrolidone, 1-hexyl-2-pyrrolidone, 1-hexyl-4-methyloxycarbonyl-2-pyrrolidone, 1-(2-hydroxyethyl)pyrrolidone, 3-hydroxy-N-methyl-2-pyrrolidone, and 1-lauryl-4-methyloxycarbonyl-2-pyrrolidone.

4. The composition of claim 3, wherein the skin permeation enhancer further comprises an auxiliary skin permeation enhancer.

5. The composition of claim 4, wherein the auxiliary skin permeation enhancer is at least one non-ionic surfactant.

6. The composition of claim 1, wherein the anti-irritant agent is at least one selected from the group consisting of squalene, squalane, avocado oil, tocopherol, polyvinyl pyrrolidone, hialulonic acid, aloevera gel, spingosine, betaglucan, rosemary oil, and alantoin.

7. The composition of claim 1, wherein the thickener is at least one selected from the group consisting of waxes and their derivatives; metallic salts of stearic acids; polyethylene; polyethylene glycol of high molecular weight; and polyethylene oxide.

* * * * *